United States Patent [19]

DeMarinis et al.

[11] 3,965,099

[45] *June 22, 1976

[54] CEPHALOSPORIN ESTERS WITH ANTIBACTERIAL ACTIVITY

[75] Inventors: Robert M. DeMarinis, King of Prussia; John R. E. Hoover, Glenside, both of Pa.

[73] Assignee: SmithKline Corporation, Philadelphia, Pa.

[ * ] Notice: The portion of the term of this patent subsequent to Aug. 6, 1991, has been disclaimed.

[22] Filed: June 26, 1974

[21] Appl. No.: 483,189

[52] U.S. Cl. .............................. 260/243 C; 424/246
[51] Int. Cl.$^2$............... C07D 501/50; A61K 31/545
[58] Field of Search ............................. 260/243 C

[56] References Cited
UNITED STATES PATENTS

| | | | |
|---|---|---|---|
| 3,488,730 | 1/1970 | Stephens | 260/243 C |
| 3,655,658 | 4/1972 | Godtfredson | 260/243 C |
| 3,708,479 | 1/1973 | Welch et al. | 260/243 C |
| 3,828,037 | 8/1974 | DeMarinis et al. | 260/243 C |
| 3,856,785 | 12/1974 | Breuer | 260/243 C |

FOREIGN PATENTS OR APPLICATIONS

| | | | |
|---|---|---|---|
| 802,199 | 1/1974 | Belgium | 260/243 C |
| 2,228,670 | 1/1973 | Germany | |
| 2,230,620 | 12/1972 | Germany | |
| 7,310,098 | 2/1973 | Japan | |
| 7,238,996 | 12/1972 | Japan | |

OTHER PUBLICATIONS

Johnston, Chemical Abstracts, vol. 79 18,737m, (1973).

*Primary Examiner*—Alton D. Rollins
*Assistant Examiner*—Diana G. Rivers
*Attorney, Agent, or Firm*—Stuart R. Suter; William H. Edgerton; Alan D. Lourie

[57] ABSTRACT

Esters of 7-trifluoromethylmercaptoacetamido-3-(1-methyltetrazol-5-ylthiomethyl)-3-cephem-4-carboxylic acid are prepared. These compounds are antibacterial agents.

14 Claims, No Drawings

CEPHALOSPORIN ESTERS WITH ANTIBACTERIAL ACTIVITY

This invention relates to new esters of cephalosporin acids which have antibacterial activity. In particular, the compounds are esters of 7-trifluoromethylmercaptoacetamido-3-(1-methyltetrazol-5-ylthiomethyl)-3-cephem-4-carboxylic acid.

The compounds of this invention are illustrated by the following structural formula:

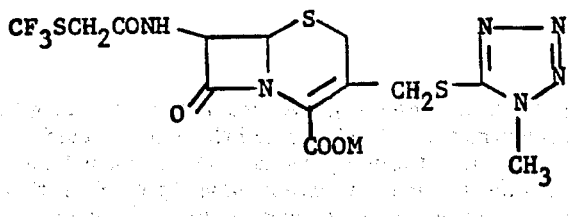

wherein

M is $\underset{R_1}{CHOCO(CH_2)_nR}$, $\underset{R_1}{CHOCO(CH_2)_n}\underset{NR_4R_5}{\overset{R_2}{\underset{|}{C}}-R_3}$, $\underset{R_1}{CHXCOOR_6}$ or indanyl;

$n$ is 0 to 4;

$R$ is hydrogen, alkyl having 1 to 8 carbon atoms, cycloalkyl, phenyl, lower phenalkyl, pyridyl, thienyl, or pyrrolyl;

$R_1$ is hydrogen, methyl, or ethyl;

$R_2$ and $R_3$ are each hydrogen, alkyl having 1 to 6 carbon atoms, phenyl, pyridyl, or thienyl;

$R_4$ and $R_5$ are each hydrogen or alkyl having 1 to 4 carbon atoms;

$R_6$ is alkyl having 1 to 4 carbon atoms, phenyl, lower phenalkyl, pyridyl, thiadiazolyl, amino, or lower alkylamino;

$x$ is nitrogen or oxygen; and each phenyl or phenalkyl group is unsubstituted or substituted with one or two substituents selected from the group consisting of alkyl having 1 to 6 carbon atoms, alkoxy having 1 to 4 carbon atoms, hydroxy, amino, $NHR_1$, $N(R_1)_2$, nitro, fluoro, chloro, bromo, or carboxy.

In particular, preferred M groups are acyloxymethyl esters such as acetoxymethyl, 1-acetoxyethyl, propionyloxymethyl or pivaloyloxymethyl. M may also represent benzoyloxymethyl, 4-aminobenzoyloxymethyl, phenylacetoxymethyl, 2-pyridylacetoxymethyl, 3-pyridylacetoxymethyl, 2-pyridylcarbonyloxymethyl, 4-pyridylcarbonyloxymethyl or 2-thienylacetoxymethyl or an analogous 1-acyloxyethyl ester.

Particularly preferred M groups are those containing an amino acid residue. Examples include glycyloxymethyl, phenylglycyloxymethyl, alanyloxymethyl, β-alanyloxymethyl, valyloxymethyl, p-hydroxyphenylglycyloxymethyl, 2-thienylglycyloxymethyl, or other natural amino acids.

When M is a $CHR_1NHCOOR_6$ or $CHR_1OCOOR_6$ radical, preferred groups are those where $R_1$ is hydrogen or methyl and $R_6$ is methyl, ethyl, 4-pyridylmethyl, methylaminomethyl, 2-aminoethyl, 2-methylaminoethyl, indanyl, or 1,2,3-thiadiazol-5-yl.

In addition, a preferred ester is the indanyl ester, in particular 5-indanyl.

When the ester sidechain contains an asymmetric carbon atom there can exist two optical isomers. Each diasteromer as well as mixtures of the diasteromers are within the scope of the invention.

The compounds of this invention are prepared by methods known in the art or disclosed herein. One method involves treating the haloalkyl ester of the cephalosporin with an alkali metal salt of the appropriate acid. This is illustrated in Scheme I as process A. Chloro, bromo, or iodo are useful as the halo radical in this process. Sodium or potassium are the alkali metal salts of choice.

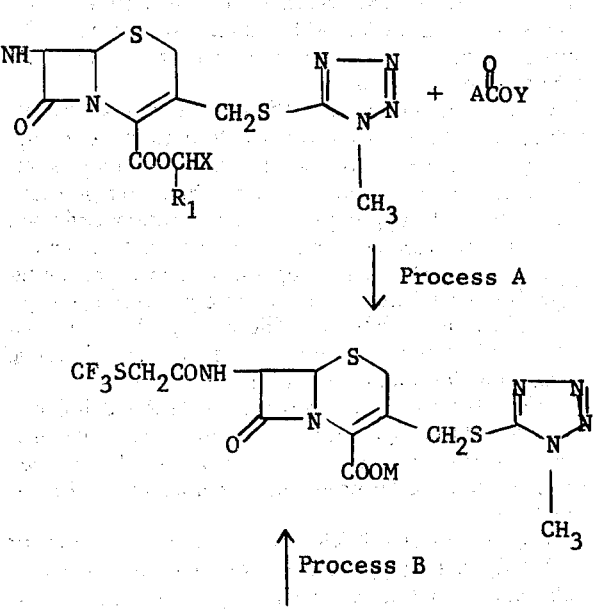

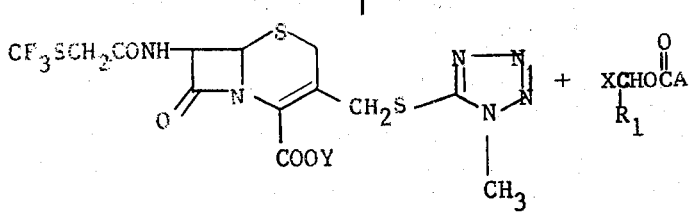

X is halo; Y is alkali metal ion

SCHEME I

Alternatively, the compounds may be prepared as set out in Scheme I as process B. This process involves treating the alkali metal salt of the cephalosporin acid with the haloalkyl ester of the appropriate side chain acid. Again potassium and sodium are useful salts and chloro, bromo or iodo may be used as the halogen.

The starting materials are commercially available, known or prepared by methods known in the art. 7-Trifluoromethylmercaptoacetamido-3-(1-methyltetrazol-5-ylthiomethyl)-3-cephem-4-carboxylic acid and its sodium salt are prepared as described in Belgian Pat. No. 802,199. Treatment of the sodium salt with chloroiodomethane gives the chloromethyl ester which may be used directly or may be treated with sodium iodide in acetone to give the iodomethyl ester.

The side chain acids or their halomethyl esters are known or prepared by known methods. Many acids and esters are disclosed in U.S. Pat. Nos. 3,655,658 and 3,728,334 and Netherlands Pat. Nos. 7,303,435 and 7,303,483. Treatment of the alkali metal salts of the acids with chloroiodomethane gives the chloromethyl ester. Those also may be converted to the iodomethyl ester by treatment with sodium iodide as described above.

Compounds where $R_1$ is methyl or ethyl are prepared by similar processes as outlined above using the $\alpha$-haloethyl or $\alpha$-halopropyl esters of the starting materials. These are prepared using 1,1-dihaloethanes, and 1,1-dihalopropanes such as 1-chloro-1-bromoethane and 1-chloro-1-iodopropane.

Any free amino groups in the side chain acid may be protected with an easily removable amino protecting group prior to being converted to the halomethyl ester or treated with the cephalosporin halomethyl ester. These protecting groups include t-butoxycarbonyl, trichloroethoxycarbonyl, benzyloxycarbonyl, or similar groups commonly used in peptide synthesis. The methods of preparing and removing these protecting groups are well known in the art. The choice of the proper group and proper conditions to remove the protecting group is within the ability of one skilled in the art.

The indanyl ester is prepared by reacting indanyl alcohol and the cephalosporin acid in the presence of a coupling reagent such as dicyclohexylcarbodiimide. Other standard ester preparation methods may also be employed.

When the ester side chain contains a free amino or carboxylic acid group salts of non-toxic pharmaceutically acceptable acids or bases can be prepared by standard methods. These salts are also within the scope of this invention.

The compounds of this invention have broad spectrum antibacterial activity against a variety of gram-positive and gram-negative organisms. For example, acetoxymethyl 7-trifluoromethylmercaptoacetamido-3-(1-methyltetrazol-5-ylthiomethyl)-3-cephem-4-carboxylate (I) and L-valyloxymethyl 7-trifluoromethylmercaptoacetamido-3-(1-methyltetrazol-5-ylthiomethyl)-3-cephem-4-carboxylate (II) had minimum inhibitory concentrations ranging from 0.8 to greater than 200 $\mu$g/ml in standard in vitro agar inclusion tests. Compound I had an $ED_{50}$ of 13.7 mg/kg on subcutaneous administration and 18.5 mg/kg on oral administration to E. coli infected mice. Compound II on subcutaneous administration had an $ED_{50}$ of 8.8 mg/kg against E. coli infected mice and 4.9 against Kleb. pneumonia infected mice and on oral administration an $ED_{50}$ of >50 and 42 mg/kg against E. coli and Kleb. pneumonia, respectively.

The compounds are formulated and administered parenterally as sterile aqueous solutions or suspensions or orally as tablets, capsules, or suspensions. The dose varies with the patient and infection being treated; however, in general the daily dose ranges from 1 to 6 grams which may be divided.

The following examples are presented to illustrate the invention but are not to be construed as limiting the scope thereof.

PREPARATION 1

To a solution of sodium 7-trifluoromethylmercaptoacetamido-3-(1-methyltetrazol-5-ylthiomethyl)-3-cephem-4-carboxylate (9.8 g, 0.02 mol) in dimethylformamide (DMF) (20 ml) is added 1-chloro-1-iodoethane (5 g) and the reaction is stirred at room temperature for 24 hours. The mixture is diluted with water and the aqueous solution is extracted with ether. The extracts are washed with 10% NaOH and then water. The dried organic layer is evaporated in vacuo to give the 1-chloroethyl ester.

The chloroethyl ester (10 mmol) is dissolved in acetone (50 ml) and then sodium iodide (20 mmol) is added. The reaction is stirred at room temperature for 18 hours, filtered and evaporated to give the 1-iodoethyl ester.

The iodomethyl ester is prepared analogous to the above by using chloroiodomethane.

PREPARATION 2

N-t-butoxycarbonyl-L-valine (4.35 g) is dissolved in DMF (20 ml) and chloroiodomethane (30 g) is added followed by triethylamine (3 g). The solution is stirred at room temperature for 20 hours, diluted with water (150 ml) and extracted with ether. The extracts are washed with 10% NaOH and then water, dried and evaporated to give the chloromethyl ester which is vacuum distilled.

The chloromethyl ester (2.65 g, 10 mmol) is treated with sodium iodide (3.0 g, 20 mmol) in acetone (50 ml) at room temperature overnight. The reaction is filtered and the filtrate is evaporated to give a residue which is partitioned between ether and water. The ether phase is dried and evaporated to give the iodomethyl ester of N-t-butoxycarbonylvaline.

EXAMPLE 1

To a cold solution of sodium 7-trifluoromethylmercaptoacetamido-3-(1-methyltetrazol-5-ylthiomethyl)-3-cephem-4-carboxylate (738 mg, 1.5 mmol) in dry DMF (10 ml) is added a solution of bromomethyl acetate (253 mg, 1.65 mmol) in DMF (1 ml). The reaction is stirred for 30 minutes at 0°C and 90 minutes at room temperature. The reaction is diluted with water and the aqueous mixture is extracted with ethyl acetate. The extracts are washed with water, dried and evaporated to give acetoxymethyl 7-trifluoromethylmercaptoacetamido-3-(1-methyltetrazol-5-ylthiomethyl)-3-cephem-4-carboxylate. The product is dissolved in ethyl acetate and is precipitated by the addition of petroleum ether.

When chloromethyl pivalate is substituted for bromomethyl acetate in the above procedure, pivaloyloxymethyl 7-trifluoromethylmercaptoacetamido-3-(1-methyltetrazol-5-ylthiomethyl)-3-cephem-4-carboxylate is obtained.

EXAMPLE 2

A solution of sodium 7-trifluoromethylmercaptoacetamido-3-(1-methyltetrazol-5-ylthiomethyl)-3-cephem-4-carboxylate (2 mmol) and the iodomethyl ester of N-t-butoxycarbonyl-L-valine (2.2 mmol) in DMF (20 ml) is stirred at room temperature for 2 hours. The reaction is poured into water and extracted with ether. The extracts are washed with water, dried, and evaporated to give the N-protected ester which is chromatographed on silica gel using 95:5 ether-ethyl acetate as eluant.

The product is treated with trifluoroacetic acid at room temperature for 30 minutes. The solution is evaporated and the residue is triturated with ether to give the trifluoroacetate salt of L-valyloxymethyl 7-trifluoromethylmercaptoacetamido-3-(1-methyltetrazol-5-ylthiomethyl)-3-cephem-4-carboxylate.

EXAMPLE 3

Substitution of the iodomethyl esters of the t-butoxycarbonyl derivatives of glycine, alanine, β-alanine, phenylglycine, p-hydroxyphenylglycine, or 2-thienylglycine for the valine derivative in Example 2 gives the following compounds:

Glycyloxymethyl 7-trifluoromethylmercaptoacetamido-3-(1-methyltetrazol-5-ylthiomethyl)-3-cephem-4-carboxylate Alanyloxymethyl 7-trifluoromethylmercaptoacetamido-3-(1-methyltetrazol-5-ylthiomethyl)-3-cephem-4-carboxylate β-Alanyloxymethyl 7-trifluoromethylmercaptoacetamido-3-(1-methyltetrazol-5-ylthiomethyl)-3-cephem-4-carboxylate Phenylglycyloxymethyl 7-trifluoromethylmercaptoacetamido-3-(1-methyltetrazol-5-ylthiomethyl)-3-cephem-4-carboxylate p-Hydroxyphenylglycyloxymethyl 7-trifluoromethylmercaptoacetamido-3-(1-methyltetrazol-5-ylthiomethyl)-3-cephem-4-carboxylate 2-Thienylglycyloxymethyl 7-trifluoromethylmercaptoacetamido-3-(1-methyltetrazol-5-ylthiomethyl)-3-cephem-4-carboxylate.

EXAMPLE 4

To a solution of 7-trifluoromethylmercaptoacetamido-3-(1-methyltetrazol-5-ylthiomethyl)-3-cephem-4-carboxylic acid (4.70 g, 0.01 mol) and 5-indanol (1.34 g, 0.01 mol) in tetrahydrofuran is added dicyclohexylcarbodiimide (2.06 g, 0.01 mol) and the reaction is stirred for 4 hours at room temperature. The solid urea is collected and washed with tetrahydrofuran and the filtrate is evaporated to give 5-indanyl 7-trifluoromethylmercaptoacetamido-3-(1-methyltetrazol-5-ylthiomethyl)-3-cephem-4-carboxylate.

EXAMPLE 5

When the iodomethyl esters of benzoic acid, phenylacetic acid, 2-pyridylacetic acid, 2-thienylacetic acid, or p-nitrobenzoic acid, which are prepared by an analogous procedure as in Preparation 2, are substituted for bromomethyl acetate in Example 1 the following compounds are obtained:

Benzoyloxymethyl 7-trifluoromethylmercaptoacetamido-3-(1-methyltetrazol-5-ylthiomethyl)-3-cephem-4-carboxylate Phenylacetoxymethyl 7-trifluoromethylmercaptoacetamido-3-(1-methyltetrazol-5-ylthiomethyl)-3-cephem-4-carboxylate 2-Pyridylacetoxymethyl 7-trifluoromethylmercaptoacetamido-3-(1-methyltetrazol-5-ylthiomethyl)-3-cephem-4-carboxylate 2-Thienylacetoxymethyl 7-trifluoromethylmercaptoacetamido-3-(1-methyltetrazol-5-ylthiomethyl)-3-cephem-4-carboxylate p-Nitrobenzoyloxymethyl 7-trifluoromethylmercaptoacetamido-3-(1-methyltetrazol-5-ylthiomethyl)-3-cephem-4-carboxylate.

EXAMPLE 6

The p-nitrobenzoyloxymethyl ester (0.01 mol) from Example 5 is hydrogenated in methanol (50 ml) with 10% Pd on carbon at catalyst until hydrogen uptake stops. The solution is filtered and evaporated to give p-aminobenzoyloxymethyl 7-trifluoromethylmercaptoacetamido-3-(1-methyltetrazol-5-ylthiomethyl)-3-cephem-4-carboxylate.

EXAMPLE 7

A solution of 1-iodoethyl 7-trifluoromethylmercaptoacetamido-3-(1-methyltetrazol-5-ylthiomethyl)-3-cephem-4-carboxylate (0.01 mol) in dry DMF is treated at room temperature with the t-butoxycarbonyl derivative of glycine sodium salt (0.011 mol) for 4 hours. The reaction is diluted with water and extracted with ether. The extracts are washed with water, dried and evaporated to a residue. The residue is stirred with trifluoroacetic acid at room temperature for 30 minutes. The solution is evaporated and the residue is triturated with ether to give the trifluoroacetate salt of 1-glycyloxyethyl 7-trifluoromethylmercaptoacetamido-3-(1-methyltetrazol-5-ylthiomethyl)-3-cephem-4-carboxylate.

EXAMPLE 8

Substitution of the sodium salt of the t-butoxycarbonyl derivative of the phenylglycine, alanine, β-alanine, valine, p-hydroxyphenylglycine or 7-thienylglycine is substituted for the glycine derivative in Example 7 the following compounds are obtained:

1-phenylglycyloxyethyl 7-trifluoromethylmercaptoacetamido-3-(1-methyltetrazol- 5-ylthiomethyl)-3-cephem-4-carboxylate 1-alanyloxyethyl 7-trifluoromethylmercaptoacetamido-3-(1-methyltetrazol-5-ylthiomethyl)-3-cephem-4-carboxylate 1-β-alanyloxyethyl 7-trifluoromethylmercaptoacetamido-3-(1-methyltetrazol-5-ylthiomethyl)-3-cephem-4-carboxylate 1-valyloxyethyl 7-trifluoromethylmercaptoacetamido-3-(1-methyltetrazol-5-ylthiomethyl)-3-cephem-4-carboxylate 1-(p-hydroxyphenylglycyl)ethyl 7-trifluoromethylmercaptoacetamido-3-(1-methyltetrazol-5-ylthiomethyl)-3-cephem-4-carboxylate 1-(2-thienylglycyloxy)ethyl 7-trifluoromethylmercaptoacetamido-3-(1-methyltetrazol-5-ylthiomethyl)-3-cephem-4-carboxylate.

EXAMPLE 9

A solution of sodium 7-trifluoromethylmercaptoacetamido-3-(1-methyltetrazol-5-ylthiomethyl)-3-cephem-4-carboxylate (0.007 mol) and N-chloromethyl ethyl carbamate (0.96 g, 0.007 mol) in DMF (25 ml) is stirred for 4 hours and then worked up as in Example 1 to give ethoxycarbonylaminomethyl 7-trifluoromethylmercaptoacetamido-3-(1-methyltetrazol-5-ylthiomethyl)-3-cephem-4-carboxylate.

EXAMPLE 10

Chloromethyl methyl carbonate (0.02 mol) is reacted with sodium 7-trifluoromethylmercaptoacetamido-3-(1-methyltetrazol-5-ylthiomethyl)-3-cephem-4-carboxylic acid (0.01 mol) in DMF for 20 hours. On work up as described in Example 1, methoxycarbonyloxymethyl 7-trifluoromethylmercaptoacetamido-3-(1-methyltetrazol-5-ylthiomethyl)-3-cephem-4-carboxylate is obtained.

EXAMPLE 11

When β-azidoethyl chloromethyl carbonate is substituted for chloromethyl methyl carbonate in Example 10, the β-azidoethoxycarbonyloxymethyl ester is obtained which is hydrogenated in methanol with Pd on carbon as catalyst. Filtration and evaporation of the filtrate gives β-aminoethoxycarbonyloxymethyl 7-trifluoromethylmercaptoacetamido-3-(1-methyltetrazol-5-ylthiomethyl)-3-cephem-4-carboxylate.

EXAMPLE 12

An antibacterial capsule is comprised of the following components:

| | |
|---|---|
| cephalosporin | 500 mg. |
| lactose | 250 mg. |
| magnesium stearate | 75 mg. |

Any compound within the scope of this invention may be used as the cephalosporin component.

Any compound within the scope of this invention which contains a basic moiety or an acid moiety can be converted to a pharmaceutically acceptable salt by standard methods. An injectable pharmaceutical composition is prepared by dissolving 500 mg of the salt in sterile water or sterile normal saline solution.

We claim:

1. A compound of the formula

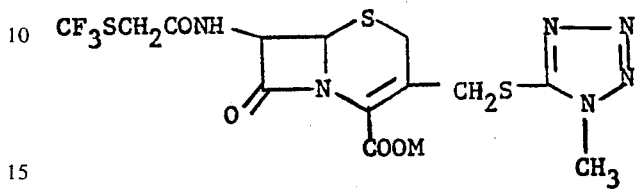

wherein:

M is 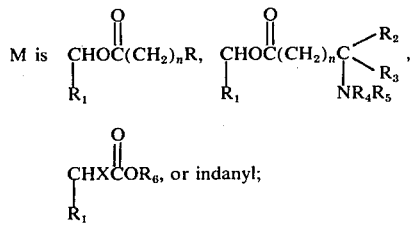

$n$ is 0 to 4;

R is hydrogen, alkyl having 1 to 8 carbon atoms, cycloalkyl of 3 to 6 carbon atoms, phenyl, $C_1$–$C_4$ phenalkyl, pyridyl, thienyl, or pyrrolyl;

$R_1$ is hydrogen, methyl or ethyl;

$R_2$ and $R_3$ are each hydrogen, alkyl having 1 to 6 carbon atoms, phenyl, pyridyl, or thienyl;

$R_4$ and $R_5$ are each hydrogen or alkyl of 1 to 4 carbon atoms;

$R_6$ is alkyl having 1 to 4 carbon atoms, phenyl, phenalkyl having 1 to 4 carbon atoms, pyridyl, thiadiazolyl, amino or $C_1$–$C_4$ alkylamino;

X is NH or oxygen; and each phenyl group is unsubstituted or substituted with one or two substituents selected from the group consisting of alkyl having 1 to 6 carbon atoms, alkoxy having 1 to 4 carbon atoms, hydroxy, amino, $NHR_1$, $N(R_1)_2$, nitro, fluoro, chloro, bromo, or carboxy.

2. A compound as claimed in claim 1 where M is

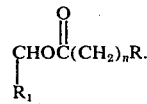

3. A compound as claimed in claim 1 where M is

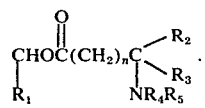

4. A compound as claimed in claim 1 where M is

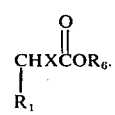

5. A compound as claimed in claim 2 where n is 0 to 1 and $R_1$ is hydrogen.

6. A compound as claimed in claim 5 being the compound acetoxymethyl 7-trifluoromethylmercaptoacetamido-3-(1-methyltetrazol-5-ylthiomethyl)-3-cephem-4-carboxylate.

7. A compound as claimed in claim 5 being the compound pivalyloxymethyl 7-trifluoromethylmercaptoacetamido-3-(1-methyltetrazol-5-ylthiomethyl)-3-cephem-4-carboxylate.

8. A compound as claimed in claim 5 being the compound p-aminobenzoyloxymethyl 7-trifluoromethylmercaptoacetamido-3-(1-methyltetrazol-5-ylthiomethyl)-3-cephem-4-carboxylate.

9. A compound as claimed in claim 3 where n is 0 or 1 and $R_2$, $R_4$ and $R_5$ are hydrogen.

10. A compound as claimed in claim 9 being the compound glycyloxymethyl 7-trifluoromethylmercaptoacetamido-3-(1-methyltetrazol-5-ylthiomethyl)-3-cephem-4-carboxylate.

11. A compound as claimed in claim 9 being the compound phenylglycyloxymethyl 7-trifluoromethylmercaptoacetamido-3-(1-methyltetrazol-5-ylthiomethyl)-3-cephem-4-carboxylate.

12. A compound as claimed in claim 9 being the compound valyloxymethyl 7-trifluoromethylmercaptoacetamido-3-(1-methyltetrazol-5-ylthiomethyl)-3-cephem-4-carboxylate.

13. A compound as claimed in claim 9 being the compound 2-thienylglycyloxymethyl 7-trifluoromethylmercaptoacetamido-3-(1-methyltetrazol-5-ylthiomethyl)-3-cephem-4-carboxylate.

14. A compound as claimed in claim 1 being the compound 5-indanyl 7-trifluoromethylmercaptoacetamido-3-(1-methyltetrazol-5-ylthiomethyl)-3-cephem-4-carboxylate.

* * * * *